United States Patent [19]

Shiraishi et al.

[11] Patent Number: 4,853,403
[45] Date of Patent: Aug. 1, 1989

[54] 3-PHENYLTHIOMETHYLSTYRENE DERIVATIVE, PROCESS FOR PREPARING THE SAME, AND ANTIALLERGIC AGENT AND TYROSINEKINASE INHIBITING AGENT CONTAINING THE SAME

[75] Inventors: Tadayoshi Shiraishi, Takasago; Naohiro Imai, Kakogawa; Takeshi Domoto, Kakogawa; Keiji Kameyama, Kakogawa; Ikuo Katsumi; Takayoshi Hidaka, both of Kobe; Kazunori Hosoe, Takasago; Kiyoshi Watanabe, Akashi, all of Japan

[73] Assignee: Kanegafuchi Kagaku Kogyo Kabushiki Kaisha, Osaka, Japan

[21] Appl. No.: 890,034

[22] Filed: Jul. 28, 1986

[30] Foreign Application Priority Data

Jul. 29, 1985 [JP] Japan .................................. 60-167998
Jul. 18, 1986 [JP] Japan .................................. 61-169303

[51] Int. Cl.⁴ ................. A61K 31/085; A61K 31/095; A61K 31/04; A61K 31/135; A61K 31/19; A61K 31/215; A61K 31/275; A61K 31; A61K 365; A61K 31/40; A61K 31/41; C07D 231/08; C07D 207/12; C07D 307/32; C07C 149/40; C07C 147/107; C07C 143/67; C07C 147/13; C07C 147/11

[52] U.S. Cl. .................................. 514/404; 514/424; 514/473; 514/570; 514/618; 514/713; 548/321; 548/361; 548/543; 549/323; 558/401; 560/9; 560/11; 560/12; 560/13; 562/426; 562/429; 562/430; 564/162

[58] Field of Search ................. 548/361, 543, 321; 549/323; 558/401; 560/9, 11, 12, 13; 562/429, 430, 426; 564/162; 514/404, 424, 473, 570, 618, 713

[56] References Cited

U.S. PATENT DOCUMENTS

Re. 29,467  11/1977  Nussim et al. ..................... 558/404
3,940,422   2/1976   Harita et al. ..................... 549/441

OTHER PUBLICATIONS

Chemische Berichte, 95, 483–486 (1962).

*Primary Examiner*—Mary C. Lee
*Assistant Examiner*—J. Richter
*Attorney, Agent, or Firm*—Armstrong, Nikaido, Marmelstein & Kubovcik

[57] ABSTRACT

A 3-phenylthiomethylstyrene derivative having the general formula (1):

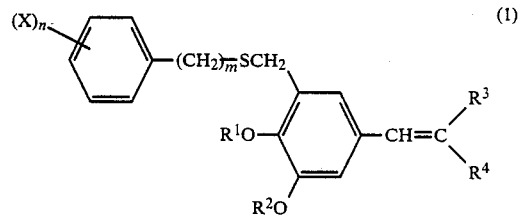

or salt thereof with a base, when X is hydroxyl group, $R^1$ is hydrogen atom or $R^2$ is hydrogen atom, a process for preparing the 3-phenylthiomethylstyrene derivative (1), and an antiallergic agent and a tyrosinekinase inhibiting agent containing the 3-phenylthiomethylstyrene derivative (1) as an effective component. The compound (1) of the present invention is a useful intermediate for preparing various organic compounds, and has excellent antiallergic and tyrosinekinase inhibiting activities.

34 Claims, No Drawings

3-PHENYLTHIOMETHYLSTYRENE DERIVATIVE, PROCESS FOR PREPARING THE SAME, AND ANTIALLERGIC AGENT AND TYROSINEKINASE INHIBITING AGENT CONTAINING THE SAME

BACKGROUND OF THE INVENTION

The present invention relates to a novel 3-phenylthiomethylstyrene derivative which has antiallergic and tyrosinekinase inhibiting activities and is useful as an intermediate for preparing various organic compounds or a salt thereof with a base when the derivative can form a salt, a process for preparing the same, and an antiallergic agent and a tyrosinekinase inhibiting agent containing the same as an effective component.

The compound of the present invention is a novel compound which has not yet been reported in the literature and is first synthesized by the present inventors.

SUMMARY OF THE INVENTION

The present inventors have found that a novel 3-phenyltiomethylstyrene derivative of the present invention is a useful intermediate for preparing various organic compounds and has itself antiallergic and tyrosinekinase inhibiting activities.

According to the present invention, there is provided 3-phenylthiomethylstyrene derivative having the general formula (1):

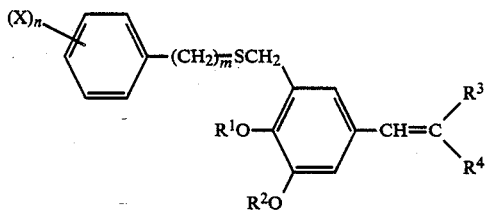

wherein X is hydrogen atom, an alkoxyl group represented by the formula: $R^5O$ in which $R^5$ is an alkyl group having 1 to 3 carbon atoms, an alkyl group having 1 to 5 carbon atoms, nitro group, amino group, hydroxyl group, a halogen atom or an alkoxycarbonyl group represented by the formula: $COOR^6$ in which $R^6$ is an alkyl group having 1 to 3 carbon atoms; $R^1$ is hydrogen atom, an alkyl group having 1 to 3 carbon atoms or an acyl group represented by the formula: $R^7CO$ in which $R^7$ is phenyl group or an alkyl group having 1 to 3 carbon atoms; $R^2$ is hydrogen atom or an alkyl group having 1 to 5 carbon atoms; $R^3$ is a group represented by the formula: $COOR^8$ in which $R^8$ is hydrogen atom or an alkyl group having 1 to 4 carbon atoms or an amide group; $R^4$ is cyano group or an alkylsulfonyl group represented by the formula: $R^9SO_2$ in which $R^9$ is an alkyl group having 1 to 4 carbon atoms; or $R^3$ and $R^4$ when taken together represent a group represented by the formula:

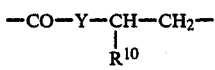

in which $R^{10}$ is hydrogen atom or an alkyl group having 1 to 4 carbon atoms and Y is oxygen atom or NH, a group represented by the formula:

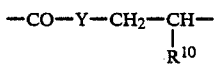

in which $R^{10}$ and Y are as defined above or a group represented by the formula:

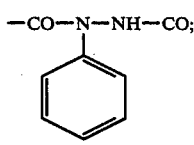

n is an integer of 1 to 5 when X is a halogen atom or is 1 when X is a group other than the halogen atom; and m is 0 or an integer of 1 to 3, or a salt thereof.

Also, according to the present invention, there is provided a process for preparing the 3-phenylthiomethylstyrene derivative (1).

Further, according to the present invention, there is provided an antiallergic agent or a tyrosinekinase inhibiting agent containing the 3-phenylthiomethylstyrene derivative as an effective component.

DETAILED DESCRIPTION

Among the compound having the general formula (1) of the present invention, the compound can form a salt with a base when X is hydroxyl group, $R^1$ is hydrogen atom or $R^2$ is hydrogen atom. The salt of the present invention may be any which can be formed from the compound of the present invention and the base. Examples of the salt are, for instance, a salt with metal, especially an alkali metal salt, an alkaline earth metal salt and a salt with aluminum; an ammonium salt; and an amine salt, especially a salt with methylamine, ethylamine, diethylamine, triethylamine, pyrrolidine, piperdine, morpholine, hexamethyleneimine, aniline or pyridine, and the like.

When the salts are employd for the antiallergic agent or typrosinekinase inhibiting agent, the pharmaceutically acceptable salts should be employed.

Typical examles of the compounds of the invention are shown in Table 1.

TABLE 1

| Compound No. | R¹ | R² | (X)n aryl | m | R³ | R⁴ | Molecular formula (Molecular weight) | Melting point (°C.) | Elementary analysis | | | | | |
|---|---|---|---|---|---|---|---|---|---|---|---|---|---|---|
| | | | | | | | | | C Found (%) | C Calcd. (%) | H Found (%) | H Calcd. (%) | N Found (%) | N Calcd. (%) |
| I | H | $C_2H_5$ | phenyl | 0 | $CONH_2$ | CN | $C_{19}H_{18}N_2O_3S$ (354.42) | 157 to 161 | 64.03 | 64.40 | 5.01 | 5.12 | 7.56 | 7.90 |
| II | H | $C_2H_5$ | 4-$CH_3O$-phenyl | 0 | $CONH_2$ | CN | $C_{20}H_{20}N_2O_4S$ (384.45) | 158 to 160 | 62.27 | 62.49 | 5.13 | 5.24 | 7.51 | 7.29 |
| III | H | $C_2H_5$ | 4-$NO_2$-phenyl | 0 | $CONH_2$ | CN | $C_{19}H_{17}N_3O_5S$ (399.43) | 182 to 183 | 57.28 | 57.14 | 4.38 | 4.29 | 10.27 | 10.52 |
| IV | H | $C_2H_5$ | 4-Br-phenyl | 0 | $CONH_2$ | CN | $C_{19}H_{17}N_2O_3SBr$ (433.33) | 171 to 173 | 52.31 | 52.66 | 3.74 | 3.95 | 6.13 | 6.46 |
| V | H | $C_2H_5$ | pentafluorophenyl | 0 | $CONH_2$ | CN | $C_{19}H_{13}N_2O_3SF_5$ (444.38) | 165.5 to 166 | 51.63 | 51.35 | 2.98 | 2.95 | 6.76 | 6.30 |
| VI | H | $C_2H_5$ | phenyl | 3 | $CONH_2$ | CN | $C_{22}H_{24}N_2O_3S$ (396.51) | 96.5 to 99 | 66.33 | 66.65 | 5.98 | 6.10 | 6.98 | 7.07 |
| VII | H | $C_2H_5$ | 2-$OCH_3$-phenyl | 0 | $CONH_2$ | CN | $C_{20}H_{20}N_2O_4S$ (384.45) | 149.5 to 150 | 62.67 | 62.49 | 5.28 | 5.24 | 7.43 | 7.29 |

TABLE 1-continued

| Compound No. | $R^1$ | $R^2$ | $(X)_n$ ⬡ | m | $R^3$ | $R^4$ | Molecular formula (Molecular weight) | Melting point (°C) | Elementary analysis C Found (%) | C Calcd. (%) | H Found (%) | H Calcd. (%) | N Found (%) | N Calcd. (%) |
|---|---|---|---|---|---|---|---|---|---|---|---|---|---|---|
| VIII | H | $C_2H_5$ | $CH_3O$-phenyl | 0 | $CONH_2$ | CN | $C_{20}H_{20}N_2O_4S$ (384.45) | 151 to 152 | 62.31 | 62.49 | 5.22 | 5.24 | 7.53 | 7.29 |
| IX | H | $C_2H_5$ | $CH_3$-phenyl | 0 | $CONH_2$ | CN | $C_{20}H_{20}N_2O_3S$ (368.46) | 185 to 186 | 65.10 | 65.21 | 5.39 | 5.47 | 7.47 | 7.61 |
| X | H | $C_2H_5$ | 2,6-diCl-phenyl | 0 | $CONH_2$ | CN | $C_{19}H_{16}N_2O_3SCl_2$ (423.32) | 192 to 193.5 | 53.65 | 53.91 | 3.67 | 3.81 | 6.34 | 6.62 |
| XI | H | $C_2H_5$ | 3-Cl-phenyl | 0 | $CONH_2$ | CN | $C_{19}H_{17}N_2O_3SCl$ (388.87) | 159 to 160 | 58.93 | 58.69 | 4.27 | 4.41 | 7.53 | 7.20 |
| XII | H | $CH_3$ | phenyl | 0 | $CONH_2$ | CN | $C_{18}H_{16}N_2O_3S$ (340.40) | 183 to 185 | 63.38 | 63.52 | 4.68 | 4.74 | 8.11 | 8.23 |
| XIII | $CH_3$ | $C_2H_5$ | phenyl | 0 | $CONH_2$ | CN | $C_{20}H_{20}N_2O_3S$ (368.46) | 143 to 144 | 65.29 | 65.21 | 5.49 | 5.47 | 7.50 | 7.61 |
| XIV | H | $C_2H_5$ | 4-Cl-phenyl | 0 | $CONH_2$ | CN | $C_{19}H_{17}N_2O_3SCl$ (388.87) | 166 to 167.5 | 58.58 | 58.69 | 4.47 | 4.41 | 7.38 | 7.20 |

TABLE 1-continued

| Compound No. | R¹ | R² | (X)ₙ | m | R³ | R⁴ | Molecular formula (Molecular weight) | Melting point (°C.) | Elementary analysis | | | | | |
|---|---|---|---|---|---|---|---|---|---|---|---|---|---|---|
| | | | | | | | | | C Found (%) | C Calcd. (%) | H Found (%) | H Calcd. (%) | N Found (%) | N Calcd. (%) |
| XV | H | $C_2H_5$ | 4-methylphenyl | 0 | $CONH_2$ | CN | $C_{19}H_{16}N_2O_3SCl_2$ (423.32) | 135 to 136 | 54.12 | 53.91 | 3.93 | 3.81 | 6.95 | 6.62 |
| XVI | PhCO | $C_2H_5$ | 3,4-dichlorophenyl | 0 | $CONH_2$ | CN | $C_{26}H_{22}N_2O_4S$ (458.54) | 159 to 161 | 68.28 | 68.11 | 4.75 | 4.84 | 6.39 | 6.11 |
| XVII | $CH_3CO$ | $C_2H_5$ | phenyl | 0 | $CONH_2$ | CN | $C_{21}H_{20}N_2O_4S$ (396.47) | 178 to 179 | 63.74 | 63.63 | 5.07 | 5.09 | 7.25 | 7.07 |
| XVIII | H | $C_2H_5$ | 4-t-butylphenyl | 0 | $CONH_2$ | CN | $C_{23}H_{26}N_2O_3S$ (410.54) | 119 to 121 | 67.18 | 67.30 | 6.28 | 6.39 | 6.54 | 6.83 |
| XIX | H | H | phenyl | 0 | $CONH_2$ | CN | $C_{17}H_{14}N_2O_3S$ (326.37) | 185 (decomp.) | 62.31 | 62.57 | 4.18 | 4.32 | 8.84 | 8.59 |
| XX | H | $C_2H_5$ | 4-hydroxyphenyl | 0 | $CONH_2$ | CN | $C_{19}H_{18}N_2O_4S$ (370.43) | 170 to 171 | 61.39 | 61.61 | 4.73 | 4.90 | 7.21 | 7.56 |
| XXI | $CH_3CO$ | $C_2H_5$ | 2-($CO_2CH_3$)phenyl | 0 | $CONH_2$ | CN | $C_{23}H_{22}N_2O_6S$ (454.50) | 163 to 165 | 60.93 | 60.79 | 4.95 | 4.88 | 6.00 | 6.17 |

TABLE 1-continued

| Compound No. | R¹ | R² | (X)$_n$ | m | R³ | R⁴ | Molecular formula (Molecular weight) | Melting point (°C.) | Elementary analysis | | | | | |
|---|---|---|---|---|---|---|---|---|---|---|---|---|---|---|
| | | | | | | | | | C | | H | | N | |
| | | | | | | | | | Found (%) | Calcd. (%) | Found (%) | Calcd. (%) | Found (%) | Calcd. (%) |
| XXII | H | $C_2H_5$ | phenyl | 0 | $CO_2C_2H_5$ | $SO_2CH_3$ | $C_{21}H_{24}O_6S_2$ (436.54) | oil state | 57.40 | 57.79 | 5.68 | 5.54 | — | — |
| XXIII | H | $C_2H_5$ | 4-t-$C_4H_9$-phenyl | 0 | $CO_2C_2H_5$ | $SO_2CH_3$ | $C_{25}H_{32}O_6S_2$ (492.65) | oil state | 61.31 | 60.96 | 6.43 | 6.55 | — | — |
| XXIV | H | $C_2H_5$ | phenyl | 0 | —COOCH$_2$CH$_2$— | | $C_{20}H_{20}O_4S$ (356.44) | 141 to 143 | 67.52 | 67.40 | 5.61 | 5.66 | — | — |
| XXV | H | $C_2H_5$ | 3,4-diCl-phenyl | 0 | —COOCH$_2$CH$_2$— | | $C_{20}H_{18}O_4SCl_2$ (425.33) | 123.5 to 124.5 | 56.57 | 56.48 | 4.23 | 4.27 | — | — |
| XXVI | H | H | 4-$NO_2$-phenyl | 0 | —COOCH$_2$CH$_2$— | | $C_{18}H_{15}NO_6S$ (373.38) | 245 to 247 | 57.78 | 57.91 | 4.13 | 4.05 | 3.92 | 3.75 |
| XXVII | H | $C_2H_5$ | phenyl | 0 | —CONHCH$_2$CH$_2$— | | $C_{20}H_{21}NO_3S$ (355.46) | 173 to 174.5 | 67.76 | 67.58 | 6.03 | 5.96 | 3.85 | 3.94 |
| XXVIII | H | $CH_3$ | 4-$CH_3$-phenyl | 0 | —CONHCH$_2$CH$_2$— | | $C_{20}H_{21}NO_3S$ (355.46) | 191 to 192 | 67.52 | 67.59 | 5.93 | 5.96 | 3.73 | 3.94 |
| XXIX | $CH_3$ | $C_2H_5$ | 4-$CH_3O$-phenyl | 0 | —CONHCH$_2$CH$_2$— | | $C_{22}H_{25}NO_4S$ (399.51) | 159 to 160 | 66.31 | 66.15 | 6.39 | 6.31 | 3.38 | 3.51 |

TABLE 1-continued

| Compound No. | (X)ₙ― ⌬ | R¹ | R² | m | R³ R⁴ | Molecular formula (Molecular weight) | Melting point (°C.) | Elementary analysis | | | | | |
|---|---|---|---|---|---|---|---|---|---|---|---|---|---|
| | | | | | | | | C Found (%) | C Calcd. (%) | H Found (%) | H Calcd. (%) | N Found (%) | N Calcd. (%) |
| XXX | phenyl | PhCO | C₂H₅ | 0 | —CONHCH₂CH₂— | C₂₇H₂₅NO₄S (459.56) | oil state | 70.83 | 70.57 | 5.59 | 5.48 | 2.90 | 3.05 |
| XXXI | phenyl | H | C₂H₅ | 0 | —CONHN(Ph)CO— | C₂₅H₂₂N₂O₄S (446.53) | 184 to 184.5 | 67.56 | 67.25 | 4.79 | 4.97 | 6.01 | 6.27 |
| XXXII | phenyl | H | CH₃ | 0 | —CONHN(Ph)CO— | C₂₄H₂₀N₂O₄S (432.50) | 112 to 114 | 66.38 | 66.66 | 4.51 | 4.66 | 6.76 | 6.48 |
| XXXIII | 4-Br-phenyl | H | C₂H₅ | 0 | —CONHN(Ph)CO— | C₂₅H₂₁N₂O₄SBr (525.43) | 187 to 189 | 57.43 | 57.15 | 3.81 | 4.03 | 5.67 | 5.33 |
| XXXIV | phenyl | H | H | 0 | —CONHN(Ph)CO— | C₂₃H₁₈N₂O₄S (418.47) | 242 to 244 | 66.18 | 66.02 | 4.23 | 4.34 | 6.93 | 6.70 |
| XXXV | phenyl | H | n-C₄H₉ | 0 | —CONHN(Ph)CO— | C₂₇H₂₆N₂O₄S (474.58) | 141 to 143 | 68.18 | 68.34 | 5.39 | 5.52 | 6.23 | 5.90 |
| XXXVI | 4-Cl-phenyl | H | C₂H₅ | 0 | —CONHN(Ph)CO— | C₂₅H₂₁N₂O₄SCl (480.97) | 191 to 193 | 62.67 | 62.43 | 4.53 | 4.40 | 5.53 | 5.82 |

The compound having the general formula (1) of the present invention can be prepared by the following processes (a) to (d).

(a) Among the compound having the general formula (1), a compound having the general formula (2):

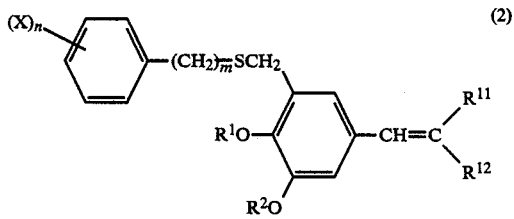

wherein X, $R^1$, $R^2$, n and m are as defined above; $R^{11}$ is a group represented by the formula: $COOR^8$ in which $R^8$ is as defined above or an amide group; $R^{12}$ is cyano group or an alkylsulfonyl group represented by the formula: $R^9SO_2$ in which $R^9$ is as defined above; or $R^{11}$ and $R^{12}$ when taken together represent a group represented by the formula:

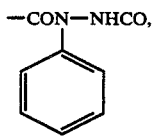

can be prepared by reacting benzaldehyde having the general formula (3):

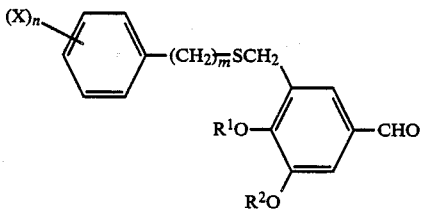

wherein X, $R^1$, $R^2$, m and n are as defined above, with a compound having the general formula (4):

   (4)

wherein $R^{11}$ and $R^{12}$ are as defined above, in the presence of a basic catalyst.

The above-mentioned reaction (a) is carried out according to the so-called Knoevenagel reaction. As the above base which can be used as the catalyst, there are exemplified ammonium, a primary amine, a secondary amine and satls thereof. Concrete examples of the base are, for instance, piperidine, pyrrolidine, ammonium acetate, piperidinium acetate, and the like.

The compound having the general formula (2), wherein X is amino group, can also be prepared by reacting the aldehyde (3), wherein X is nitro group, with the compound (4) and then reducing the obtained product in a usual manner.

(b) The compound having the general formula (1):

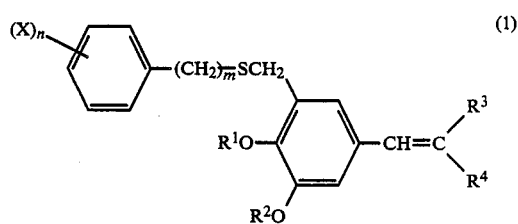

wherein X, $R^1$, $R^2$, $R^3$, $R^4$, n and m are as defined above, can be prepared, according to H. Zimmer et al. [J. Org. Chem., 24, 23 (1959); J. Het. Chem., 3, 171 (1965)] or the like, by a condensation reaction between benzalidehyde having the general formula (5):

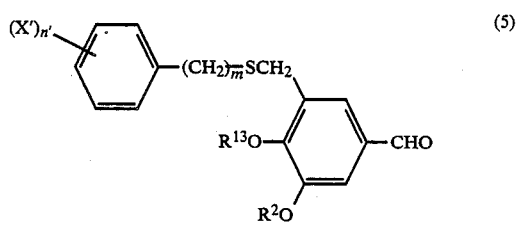

wherein $R^2$ and m are as defined above; X' is a group represented by the formula: $R^{14}O$ in which $R^{14}$ is an alkyl group having 1 to 3 carbon atoms, benzyl group, an acyl group represented by the formula: $COR^{15}$ in which $R^{15}$ is hydrogen atom or an alkyl group having 1 to 3 carbon atoms, a trialkylsilyl group, methoxymethyl group, methoxyethoxymethyl group or methylthiomethyl group; an alkyl group having 1 to 5 carbon atoms; nitro group; amino group; a halogen atom or an alkoxycarbonyl group represented by the formula: $COOR^6$ in which $R^6$ is as defined above; n' is an integer of 1 to 5 when X' is a halogen atom and is 1 when X' is a group other than the halogen atom; and $R^{13}$ is an alkyl group having 1 to 3 carbon atoms, benzyl group, an acyl group represented by the formula: $R^7CO$ in which $R^7$ is as defined above, a trialkylsilyl group, methoxymethyl group, methoxyethoxymethyl group or methylthiomethyl group, and a compound having the general formula (6):

   (6)

wherein $R^{16}$ is a group represented by the formula: $COOR^8$ in which $R^8$ is as defined above or an amide group; $R^{17}$ is cyano group or an alkylsulfonyl group represented by the formula: $R^9SO_2$ in which $R^9$ is as defined above; or $R^{16}$ and $R^{17}$ when taken together represent a group represented by the formula:

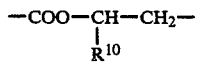

in which $R^{10}$ is hydrogen atom or an alkyl group having 1 to 4 carbon atoms, a group represented by the formula:

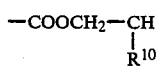

in which $R^{10}$ is as defined above, a group represented by the formula:

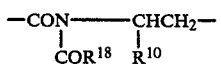

in which $R^{10}$ is as defined above and $R^{18}$ is hydrogen atom or a lower alkyl group, a group represented by the formula:

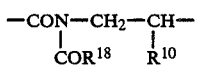

in which $R^{10}$ and $R^{18}$ are as defined above, or a group represented by the formula:

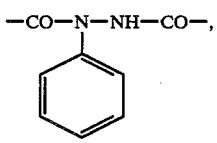

in the absence or presence of an acid or a base as a catalyst. Examples of the acid used as the catalyst are, for instance, a proton acid such as sulfuric acid, benzenesulfonic acid or p-toluenesulfonic acid, a Lewis acid such as boron trifluoride, and the like. Examples of the base used as the catalyst are, for instance, an organic base such as monoethanolamine, morpholine, pyridine or 1,3-diazabicyclo[5.4.0]undeca-7-ene, an alkali metal salt of organic acid such as sodium acetate or potassium acetate, an alkali metal hydroxide such as sodium hydroxide or potassium hydroxide, an alkali metal amide such as lithium diisopropylamide, an alkali metal alcoholate such as sodim methylate or sodium ethylate, alkali metal hydride such as sodium hydride or potassium hydride, and the like.

The compound having the general formula (1), wherein X is hydroxyl group, can also be prepared by a condensation reaction between the aldehyde having the general formula (5), wherein X' is a group represented by the formula: $R^{14}O$ in which $R^{14}$ is as defined above, and a compound having the general formula (6), followed by substitution of $R^{14}$ with hydrogen atom. When $R^{14}$ in the reaction product is alkyl, benzyl, acyl, trialkylsilyl, methoxymethyl, methoxyeoxymethyl or methylthiomethyl group due to noncatalytic reaction or catalytic reaction, the desired compound can be obtained by eliminating $R^{14}$. Similarly, the desired compound having the general formula (1), wherein $R^1$ is hydrogen atom, can also be prepared by carrying out the condensation reaction and then substituting $R^{13}$ with hydrogen atom. When $R^{13}$ in the reaction product is alkyl, benzyl, acyl, trialkylsilyl, methoxymethyl, methoxyethoxymethyl or methylthiomethyl group due to noncatalytic reaction or catalytic reaction, the desired compound can be obtained by eliminating $R^{13}$. For eliminating $R^{13}$ or $R^{14}$, when $R^{13}$ or $R^{14}$ is alkyl, methoxymyethyl, methoxyethoxymethyl or methylthiomethyl group, ether bond cleavage reaction can be employed which is carried out by using an acid such as aluminum halogenide such as aluminum chloride, boron trifluoride, hydrogen halogenide such as hydrogen bromide, or an organic acid such as trifluoroacetic acid. When $R^{13}$ or $R^{14}$ is benzyl group, catalytic reduction reaction can be employed which is carried out by using a noble metal catalyst such as palladium carbon, as well as the above-mentioned ether bond cleavage reaction. When $R^{13}$ or $R^{14}$ is acyl group, $R^{13}$ or $R^{14}$ can be eliminated by hydrolysis reaction which is carried out by using a base such as an alkali metal hydroxide such as sodium hydroxide or an alkaline earth metal hydroxide such as barium hydroxide. When $R^{13}$ or $R^{14}$ is trialkylsilyl group, $R^{13}$ or $R^{14}$ can be eliminated with water, methanol, an acid, fluorine ion, or the like.

When the reaction is carried out by employing N-acyllactam and acyl group is remained in the obtained product, acyl group can be eliminated by hydrolysis reaction using a base such as alkali metal hydroxide such as sodium hydorxide to give the desired compound.

The compound having the general formula (1), wherein X is amino group, can also be prepared by reacting the aldehyde (5), wherein X' is nitro group, with the compound (6), and then reducing the obtained product in a usual manner.

(c) The compound having the general formula (1) can be prepared, according to O. Istev et al. [Helv. Chim. Acta, 40, 1242 (1957)], G. A. Howie et al. [J. Med. Chem., 17, 840 (1974)], H. Wamhoff et al. [Synthesis, 331 (1976)], and the like, by reacting a benzaldehyde having the general formula (3):

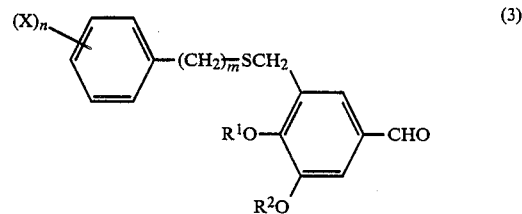

wherein X, $R^1$, $R^2$, n and m are as defined above, with a ylide having the general formula (7):

wherein Ar is an aryl group; $R^{19}$ is a group represented by the formula: $COOR^8$ in which $R^8$ is as defined above or an amide group; $R^{20}$ is cyano group or an alkylsulfonyl group represented by the formula: $R^9SO_2$ in which $R^9$ is as defined above, or $R^{19}$ and $R^{20}$ when taken together represent a group represented by the formula:

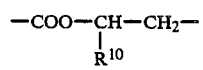

in which $R^{10}$ is as defined above, a group represented by the formula:

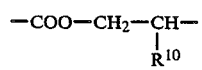

in which $R^{10}$ is as defined above, a group represented by the formula:

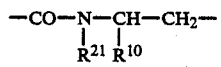

in which $R^{10}$ is as defined above and $R^{21}$ is hydrogen atom or an acyl group represented by the formula: $R^{22}CO$ in which $R^{22}$ is hydrogen atom, an alkyl group having 1 to 3 carbon atoms or an aryl group, a group prepresented by the formula:

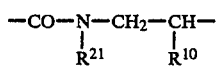

in which $R^{10}$ and $R^{21}$ are as defined above or a group represented by the formula:

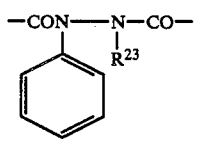

in which $R^{23}$ is hydrogen atom or an acyl group represented by the formula: $R^{24}CO$ in which $R^{24}$ is hydrogen agom, an alkyl group having 1 to 3 carbon atoms or an aryl group, and when $R^{21}$ or $R^{23}$ is acyl group, hydrolyzing the obtained product with a base such as potassium hydroxide or sodium hydroxide.

The above-mentioned reaction (c) is carried out according to the so-called Wittig reaction. For the ylide in the reaction (c), a ylide derived from a trialkyl phosphine or a triaryl arsine can also be used as well as the above-mentioned ylide (7).

The compound having the general formula (1), wherein X is amino group, can also be prepared by reacting the aldehyde having the general formula (3), wherein X is nitro group, with the ylide (7) and then reducing the obtained product in a usual manner.

(d) Among the compound having the general formula (1), a compound having the general formula (8) or (9):

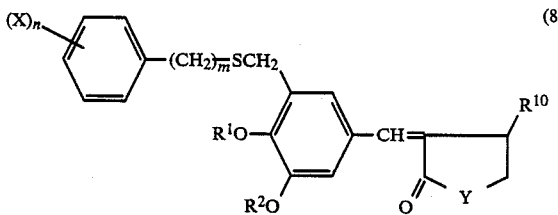

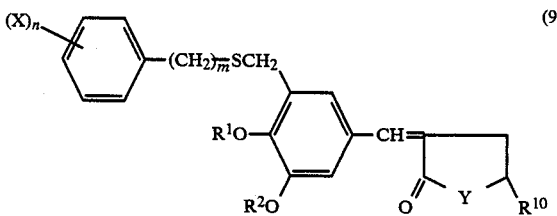

wherein X, $R^1$, $R^2$, $R^{10}$, Y, n and m are as defined above, can be prepared by reacting the above-mentioned benzaldehyde having the general formula (3) with a mixture of a compound having the general formula (10) or (11):

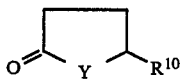

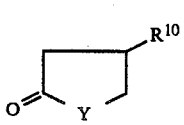

wherein $R^{10}$ and Y are as defined above, and a magnesium methyl carbonate. The magnesium methyl carbonate used herein can be prepared according to H. L. Finkbeiner et al. [J. Am. Chem. Soc., 85, 616 (1963)].

The compound having the general formula (8) or (9) can also be prepared by a reaction with the benzaldehyde having the general formula (3) wherein X is nitro group, and then reducing the obtained product in a usual manner.

3-Phenylthiomethylstyrene derivative (1) of the present invention or a salt thereof is useful as the antiallergic agents and tyrosinekinase inhibiting agents. By the tyrosinekianse inhibiting activity, the compound of the present invention can be used as the antiasmatic agents, the carcinostatic agents and the carcinogenesis preventing agents.

The antiallergic activity of the compound of the present invention was proved by the tests of biosynthesis or release of slow reacting substance of anaphylaxis (SRS-A), passive cutaneous anaphylaxis reaction and antigen-induced anaphylactic shock.

[I] SRS-A biosynthesis or release inhibitory activity

SRS-A biosynthesis or release inhibitory activity was examined according to Koda et al. [Nippon yakurigakkaishi, 66, 194(1970)] and Kono-Watanabe et al. [J. Immunology, 125, 946(1980)].

Male Hartley guinea pigs weighing 350 to 450 g were sensitized by injecting once each 1 ml of an ovalbumin (100 mg/ml) into gluteus and peritoneal cavity. Four weeks after the injection, the animals were killed and then immediately the lung was perfused with cooled Tyrode's solution to remove blood. The lung was chopped into about 2 mm fragments and 500 mg of the fragments were suspended in 4.84 ml of Tyrode's solution, to which 0.01 ml of the test compound dissolved in dimethylsulfoxide (DMSO) was added. After incubation at 37° C. for 10 minutes, 0.15 ml of an ovalbumin (10 mg/ml) was added, followed by incubation at 37° C. for 20 minutes. In control, DMSO was added and the reaction was conducted in the same manner. The reaction mixture was filtered with gauze.

An amount of SRS-A in the filtrate was bioassayed using guinea pig ileum; i.e. the ileum (length: 2 to 3 cm) was suspended in Magnus tube containing aerated Tyrode's solution at 31° C. and, after the plateau of contraction was obtained, an amount of SRS-A in the above filtrate was bioassayed in the presence of 1 μM of atropine and 1 μM of pyrilamine. Inhibition rate (%) was calculated from a contraction in control as 100.

Table 2 shows SRS-A biosynthesis and release inhibitory activity of the typical compounds of the present invention. The result proves that the compounds having the general formula (1) of the present invention greatly inhibit biosynthesis or release of the SRS-A. In Table 2, each compound No. corresponds to the compound No. in Table 1.

TABLE 2

| Compound No. | Concentration (μM) | Inhibition rate (%) |
| --- | --- | --- |
| I | 100 | 92 |
| XXII | 100 | 27 |
| XXIV | 100 | 28 |
| XXVII | 100 | 100 |
| XXXI | 100 | 59 |

[II]Inhibitory activity against homologous passive cutaneous anaphylaxis (PCA) in rats Antiserum was prepared according to I. Mota [Immunology, 7, 681(1964)] and the PCA reaction was conducted according to Maruyama et al. [Nippon yakurigakkaishi, 74, 179(1978)].

(1) Preparation of antiserum

An ovalbumin solution (2 mg/ml) was injected intramuscularly into both thighs of male Wistar rats weighing 200 to 260 g in a volume of 0.5 ml/100 g body weight, and pertussis vaccine (Bordetella pertussis, $2 \times 10^{10}$/ml, Chibaken Kessei Kenkyujo) was intraperitoneally administered at 1 ml/rat. Twelve days later, blood was taken from posterior aorta under ether anesthesia and antiserum was stored at $-80°$ C.

(2) PCA reaction

Group of 4 male Wistar rats weighing 180 to 210 g were employed. Back of the animals was shaved and each 0.05 ml of antiserum (1:32 dilution) was injected intradermally at four sites on the back. After 48 hours, 1 ml of a mixture of ovalbumin (1 mg/ml) and Evans blue (5 mg/ml) was injected intravenously into the tail. 30 Minutes later, the animals were killed under ether anesthesia. The blue-dyed area ($mm^2$) formed was measured and an inhibition rate(%) was calculated as compared with control.

Test compound suspended in a 2.5% acacia containing 0.2% Tween 80 was administered orally in a volume of 0.5 ml/100 g body weight 1 hour before the antigen. Tranilast was administered orally 30 minutes before the antigen. The result shown in Table 3 proves that the compound of the present invention shows an excellent activity.

TABLE 3

| Compound | Dose (mg/kg) | Inhibition rate (%) |
| --- | --- | --- |
| I | 100 | 21 |
| XXII | 100 | 26 |
| XXIV | 100 | 26 |
| XXVII | 100 | 25 |
| XXXI | 100 | 30 |
| tranilast | 300 | 40 |

[III] Protective effect against anaphylactic shock in actively sensitized guinea pigs Antigen-induced anaphylactic shock death was observed according to John P. Devlin [Pulmonary and Antiallergic Drugs, John Wiley & Sons, 155 (1985)].

Each 100 mg/kg of ovalbumin dissolved in physiological saline was injected into peritoneal cavity and into gluteus of male guinea pigs weighing 250 to 350 g. 3 Days later, the animals were further injected intraperitoneally with ovalbumin (100 mg/kg). Those animals were employed for testing 3 to 4 weeks after first sensitization. Actively sensitized guinea pigs were pretreated subcutaneously with pyrilamine (1 mg/kg, 30 min.) to suppress histamine-dependent response and with propanolol (1 gm/kg, 10 min.) to enhance the response induced by other than histamine before the antigen.

The animal was placed in a desiccator with a capacity of about 5 l and 0.5% aqueous solution of ovalbumin was inhaled with ultrasonic type nebulizer for five minutes. Anaphylactic shock death was observed and the animals survived for 90 minutes or more after antigen were estimated to be protected. The compounds of the present invention and antiasmatic agent were administered orally 30 minutes before the antigen inhalation. The control received vehicle alone similarly. The result shown in Table 4 proves that the compounds of the present invention shows an excellent protective effect.

TABLE 4

| Compound | Dose (mg/kg) | Protecting Effect* |
| --- | --- | --- |
| I | 100 | 2/5 |
| II | 30 | 3/4 |
| III | 100 | 1/4 |
| IV | 100 | 1/4 |
| V | 30 | 2/4 |
| VI | 100 | 1/4 |
| VII | 30 | 3/4 |
| VIII | 100 | 1/4 |
| IX | 30 | 2/4 |
| X | 30 | 3/4 |
| XI | 100 | 1/4 |
| XII | 30 | 2/4 |
| XIII | 30 | 2/4 |
| XIV | 30 | 4/4 |
| XV | 30 | 4/4 |
| XVI | 100 | 1/4 |
| XVII | 100 | 1/4 |
| XVIII | 30 | 3/4 |
| XIX | 100 | 1/4 |
| XX | 100 | 1/4 |
| XXI | 100 | 1/4 |
| XXII | 100 | 1/5 |
| XXIII | 100 | 1/4 |
| XXIV | 100 | 1/5 |
| XXV | 30 | 3/4 |
| XXVI | 100 | 1/4 |
| XXVII | 100 | 3/4 |
| XXVIII | 100 | 1/4 |
| XXIX | 100 | 1/4 |
| XXX | 30 | 2/4 |
| XXXI | 100 | 1/5 |
| XXXII | 100 | 1/4 |
| XXXIII | 30 | 3/4 |
| XXXIV | 30 | 2/4 |
| XXXV | 100 | 1/4 |
| XXXVI | 100 | 1/4 |
| tranilast | 100 | 0/4 |
| theophylline | 30 | 2/4 |
| control | — | 0/20 |

(Note)
*Number of test animal survivied/Number of test animal

Tyrosinekinase is known to be related to a carcinogenesis mechanism and this fact suggests that tryrosinekinase inhibiting agent would be useful as the carcinostatic agents or the carcinogenesis preventing agents.

Tyrosinekinase inhibitory activity of the compound of the present invention was measured by employing a method for measuring tyrosinekinase activity by G. Carpentor or by S. Cohen et al. [J. Biol. Chem., 254, 4884 (1979); J. Biol. Chem., 257, 1523 (1982)].

Cell line A-431 derived from human cancerous cell was cultured at 37° C. under the condition of 5% $CO_2$ in Dulbecco's modified Eagle medium (made by DAINIPPON PHARMACEUTICAL CO., LTD.) containing 10% fetal bovine serum, 50 μg/ml of streptomycin, 50 IU/ml of penicillin G and 50 μg/ml of canamycin. The obtained cells were treated according to the above Cohen or Graham et al. to give membrane specimen containing epidermal growth factor acceptor-tyrosinekinase complex (hereinafter referred to as "membrane specimen"). The membrane specimen was employed in the following measurement without solubilization.

Sample dissolved in dimethylsulfoxide was added to a mixture of 20 mM of N-2-hydroxyethylpyperadino-N'-2-ethanesulfonate buffer (pH 7.4), 1 mM of MnCl$_2$, 7.5 μg of bovine serum albumin and the membrane specimen (10 μg as protein). After incubation at 0° C. for 5 minutes, 100 ng of epidermal growth factor (hereinafter referred to as "EGF" was added and the mixture was further incubated at 0° C. for 15 minutes. [γ-$^{32}$P]ATP (3000 Ci/mmol, 0.1 μCi) was added to make final volume of 70 μl. After incubation at 0° C. for 15 minutes, 50 μl of the reaction solution was soaked into Wattman 3 MM filter paper and immediately the reaction was stopped by 10% trichloroacetic acid-10 mM sodium pyrophosphate aqueous solution. The filter paper was sufficiently washed with the same solution and then washed with ethanol and dried. Radioactivity present in the filter paper was measured by liquid scintillation counter (A). Similarly, radioactivity was measured in case of the reaction without EGF (B), the reaction without the sample (C), and the reaction without both EGF and the sample (D) as a control.

Tyrosinekinase inhibition rate (%) was calculated by the following equation.

$$\text{Inhibition rate (\%)} = \frac{(C-D)-(A-B)}{C-D} \times 100$$

The result shown in Table 5 proves that compound of the present invention shows excellent tyrosinekinase inhibitory activity.

TABLE 5

| Compound | Concentration (μM) | Inhibition rate (%) |
| --- | --- | --- |
| I | 100 | 100 |
| I | 10 | 100 |
| II | 10 | 42 |
| III | 10 | 42 |
| IV | 10 | 74 |
| V | 10 | 60 |
| VI | 10 | 55 |
| VII | 10 | 77 |
| VIII | 10 | 72 |
| IX | 10 | 58 |
| X | 10 | 44 |
| XI | 10 | 54 |
| XII | 10 | 86 |
| XIII | 10 | 31 |
| XIV | 10 | 29 |
| XV | 10 | 69 |
| XVI | 10 | 40 |
| XVII | 10 | 36 |
| XVIII | 10 | 37 |
| XIX | 10 | 100 |
| XX | 10 | 91 |
| XXI | 10 | 31 |
| XXII | 100 | 80 |
| XXII | 10 | 64 |
| XXIII | 10 | 40 |
| XXIV | 100 | 50 |
| XXIV | 10 | 33 |
| XXV | 10 | 27 |
| XXVI | 10 | 35 |
| XXVII | 100 | 100 |
| XXVII | 10 | 96 |
| XXVIII | 10 | 55 |
| XXIX | 10 | 30 |
| XXX | 10 | 32 |
| XXXI | 100 | 100 |
| XXXI | 10 | 92 |
| XXXII | 10 | 100 |
| XXXIII | 10 | 71 |
| XXXIV | 10 | 96 |
| XXXV | 10 | 100 |

TABLE 5-continued

| Compound | Concentration (μM) | Inhibition rate (%) |
| --- | --- | --- |
| XXXVI | 10 | 91 |

Acute toxicity test

Group of 6 female ICR mice weighing 23 to 26 g were employed. Compounds (I to XXXVI) suspended in a 2.5% acacia containing 0.2% Tween 80 were administered orally in a volume of 0.1 ml/10 g body weight. The animals were observed daily for 14 days after the administration. The LD$_{50}$ values were estimated from mortality (No. of dead mice used). The LD$_{50}$ of compounds (I to XXXVI) was estimated to be 1000 mg/kg or more, which proved a low toxicity of the compound of the present invention.

Preparations and Dosage

The antiallergic agents or tyrosinekinase inhibiting agents of the present invention can be administered orally, rectally, or parenterally in pharmaceutical dosage form, for example, tablets, capsules, fine subtilaes, syrups, suppositories, ointments, injections and the like. For an excipient of the antiallergic agents or the tyrosinekinase inhibiting agents of the present invention, organic or inorganic pharmaceutically acceptable excipient material is employed in a solid or liquid form, which is usually inactive and suited for oral, rectal or parenteral administration. Examples of such excipient are, for instance, crystalline cellulose, gelatin, lactose, starch, magnesium stearate, talc, plant or animal fat and oil, gum, polyalkylglycol and the like. A ratio of the antiallergic agents or tyrosinekinase inhibiting agents to the excipient in the formulation may vary in the range of from 0.2 to 100% by weight. The antiallergic agents or the tyrosinekinase inhibiting agents of the present invention may contain other antiallergic agents or tyrosinekinase inhibiting agents or any other drug compatible with the agents of the present invention. In this case, it is needless to say that the antiallergic agent or tyrosinekinase inhibiting agents of the present invention may not be an effective component of that formulation.

The antiallergic agents or the tyrosinekinase inhibiting agents of the present invention are administered at a dose where the desired activity is achieved without side effect. Though practical dose should be determined by a physician, the agents of the present invention is usually administered at a dose of from 10 mg to 10 g, preferably from 20 mg to 5 g for a man per day. The antiallergic agents or tyrosinekinase inhibiting agents of the present invention can be administered as a pharmaceutical formulation which contains 1 mg to 5 g, preferably 3 mg to 1 g of the effective component.

The present invention is more specifically described and explained by means of the following Examples. It is to be understood that the present invention is not limited to Examples, and various changes and modification may be made in the invention without departing from the spirit and scope thereof.

EXAMPLE 1

Preparation of the compound (I)

There were dissolved 2.90 g of 3-ethoxy-4-hydroxy-5-phenylthiomethylbenzaldehyde and 840 mg of α-cyanoacetoamide in 60 ml of benzene, to which 0.3 ml of piperidine and 1.9 ml of acetic acid were added. The mixture was heated under reflux for 5 hours in Dean-Stark apparatus while removing water produced. After cooling the reaction mixture, the deposited crystals were filtered and washed with benzene to give 2.98 g of the compound (I).
Yield: 84.1%.
Melting point: 157° to 161° C.

EXAMPLE 2

Preparation of the compound (VI)

There were added 1.37 g (4.15 mmol) of 5-(phenylpropylthiomethyl)ethylvanillin, 0.35 g (4.16 mmol) of α-cyanocinnamamide and a catalytic amount (2 to 3 drops) of piperidine to a mixed solvent of 80 ml of benzene and 1 ml of acetic acid. The mixture was heated under reflux for 4 hours in Dean-Stark apparatus. After cooling, the reaction mixture was diluted with 100 ml of chloroform and the organic layer was washed with 100 ml of water. After separating the organic layer, the organic layer was dried with anhydrous sodium sulfate and the solvent was distilled away under reduced pressure. The residue was recrystallized from benzene to give 1.38 g of the compound (VI) as light yellow needles.
Yield: 83.9%.
Melting point: 96.5° to 99° C.

EXAMPLE 3

Preparation of the compound (XIII)

There were added 0.65 g (2.15 mmol) of 3-ethoxy-4-methoxy-5-(phenylthiomethyl)benzaldehyde, 0.18 g (2.15 mmol) of α-cyanocinnamamide and a catalytic amount (2 to 3 drops) of piperidine to mixed solvent of 70 ml of benzene and 0.5 ml of acetic acid. The mixture was heated under reflux for 4 hours in Dean-Stark apparatus. After cooling, the reaction mixture was diluted with 100 ml of chloroform, and the organic layer was washed with 50 ml of water. After separating the organic layer, the organic layer was dried with anhydrous sodium sulfate and the solvent was distilled away under reduced pressure. The residue was recrystallized from benzene to give 0.49 g of the compound (XIII) as colorless needles.
Yield: 61.9%.
Melting point: 143° to 144° C.

EXAMPLE 4

Preparation of the compound (XIV)

There were added 0.97 g (3 mmol) of 5-(p-chlorophenylthiomethyl)ethylvanillin, 0.25 g (3 mmol) of α-cyanocinnamamide and a catalytic amount (2 to 3 drops) of piperidine to a mixed solvent of 80 ml of benzene and 1 ml of acetic acid. The mixture was heated under reflux for 4 hours in Dean-Stark apparatus. After cooling, the reaction mixture was diluted with 100 ml of chloroform, and the organic layer was washed with 100 ml of water. After separating the organic layer, the organic layer was dried with anhydrous sodium sulfate and the solvent was distilled away under reduced pressure. The residue was recrystallized from a mixed solvent of benzene and acetone to give 0.99 g of the compound (XIV) as light yellow needles.
Yield: 84.9%.
Melting point: 166° to 167.5° C.

EXAMPLE 5

Preparation of the compound (XVI)

There were added 0.71 g (2 mmol) of the compound (I) prepared in Example 1 and 0.3 g (2.15 mmol) of benzoyl chloride to 10 ml of pyridine. The mixture was stirred for 1 hour at room temperature. The reaction solution was poured into ice water, the deposited crystals were filtered off from the reaction mixture and the obtained crystals were recrystallized from ethanol to give 0.86 g of the compound (XVI) as colorless plates.
Yield: 93.8%.
Melting point: 159° to 161° C.

EXAMPLE 6

Preparation of the compound (XVII)

There were added 0.71 g (2 mmol) of the compound (I) prepared in Example 1 and 0.22 g (2.16 mmol) of acetic anhydride to 10 ml of pyridine, and the mixture was stirred for 2 hours at room temperature. The reaction solution was poured into ice water, the deposited crystals were filtered off from the reaction mixture and the obtained crystals were recrystallized from a mixed solvent of ethanol and acetone to give 0.7 g of the compound (XVII) as colorless needles.
Yield: 88.3%.
Melting point: 178° to 179° C.

EXAMPLE 7

Preparation of the compound (XIX)

There were added 0.39 g (1.5 mmol) of 5-phenylthiomethyl)protocatechualdehyde, 0.13 g (1.5 mmol) of α-cyanocinnamamide and a catalytic amount (1 to 2 drops) of piperidine to a mixed solvent of 50 ml of benzene and 0.5 ml of acetic acid. The mixture was heated under reflux for 4 hours in Dean-Stark apparatus. After cooling, the deposited crystals were filtered off from the reaction mixture and the obtained crystals were recrystallized from a mixed solvent of benzene and acetone to give 0.42 g of the compound (XIX) as yellow needles.
Yield: 85.9%.
Melting point: 185° C. (decomposition).

EXAMPLE 8

Preparation of the compound (XX)

There were added 0.48 g (1.6 mmol) of 5-(p-hydroxyphenylthiomethyl)ethylvanillin, 0.14 g (1.7 mmol) of α-cyanocinnamamide and a catalytic amount (2 to 3 drops) of piperidine to mixed solvent of 50 ml of benzene and 0.5 ml of acetic acid. The mixture was heated under reflux for 6 hours in Dean-Stark apparatus. After cooling, the reaction was concentrated under reduced pressure and the residue was separated and purified by silica-gel column-chromatography (eluent: chloroform:methanol=10:1). The eluent containing the desired compound (XX) was concentrated under reduced pressure and the obtained residue was recrystallized from a mixed solvent of benzene and acetone to give 0.3 g of the compound (XX) as yellow needles.
Yield: 51.4%.
Melting point: 170° to 171° C.

EXAMPLE 9

Preparation of the compound (XXII)

There were dissolved 4.35 g of 3-ethoxy-4-hydroxy-5-phenylthiomethylbenzaldehyde and 2.49 g of ethyl methanesulfonylacetate in 60 ml of benzene, to which 0.3 ml of piperidine and 0.9 ml of acetic acid were added. The mixture was heated under reflux for 8 hours in Dean-Stark extractor while removing water produced. After cooling, the reaction mixture was added with chloroform and washed with water. Then, the solvent of the organic layer was distilled away and the obtained residue was subjected to a silica-gel column-chromatography [eluent: ethyl acetate:n-hexane=2:5 (v/v)] to give 1.40 g of the compound (XXII).
Yield: 21.1%.

EXAMPLE 10

Preparation of the compound (XXIV)

There were added 5.76 g of 3-ethoxy-4-hydroxy-5-phenylthiomethylbenzaldehyde and 7.96 g of α-phospholanylidene-γ-butyrolactone to 30 ml of acetonitrile and the mixture was heated under reflux for 8 hours. After removing the solvent, the residue was crystallized from ethanol. The obtained crystals was recrystallized from ethanol to give 4.0 g of the compound (XXIV).
Yield: 56.1%.
Melting point: 141° to 143° C.

EXAMPLE 11

Preparation of the compound (XXV)

There were added 1.79 g (5 mmol) of 5-(3,4-dichlorophenylthiomethyl)ethylvanillin and 2.08 g (6 mmol) of 3-triphenylphospholanylidene)-γ-butyrolactone to 70 ml of acetonitrile and the mixture was stirred at 80° C. for a night. After cooling, the solvent was distilled away from the reaction mixture under reduced pressure and the obtained residue was separated and purified silica-gel column-chromatography (eluent:chloroform). The eluent containing the desired compound (XXV) was concentrated under reduced pressure and the obtained residue was recrystallized from ethanol to give 1.47 g of the compound (XXV) as light yellow needles.
Yield: 69.0%.
Melting point: 123.5° to 124.5° C.

EXAMPLE 12

Preparation of the compound (XXVII)

There was suspended 1.20 g of sodium hydride in 20 ml of benzene, to which a solution of 4.04 g of 4-t-butyldimethylsilyloxy-3-ethoxy-4-phenylthiomethylbenzaldehyde and 1.27 g of N-acetylpyrrolidone dissolved in 30 ml of benzene was added at 5° C. under nitrogen atmopshere. The mixture was heated to 60° C. and stirred for 2 hours. After cooling, methanol was added to the reaction mixture to decompose an excessive amount of sodium hydride, which was added with water and neutralized with 6N sulfuric acid. The solution was extracted with a mixed solvent of chloroform and ethanol and the solvent was distilled away from the obtained eluent. The residue was subjected to a silica-gel column-chromatography [eluent:ethyl acetate:n-hexane=1:1 (v/v) and ethyl acetate] with a gradient elution.

The fraction containing the desired compound (XXVII) was concentrated to give white crystals. The obtained white crystals were dissolved in 30 ml of tetrahydrofuran, to which 5 ml of a 1M solution of tetra-n-butylammonium fluoride in tetrahydrofuran was added and the mixture was stirred at room temperature for 1 hour. After the reaction mixture was added with chloroform and washed with water, the solvent of the organic layer was distilled away. The residue was crystallized from a mixed solvent of ethyl acetate and chloroform to give 980 mg of the compound (XXVII).
Yield: 27.6%.
Melting point: 173° to 174.5° C.

EXAMPLE 13

Preparation of the compound (XXXI)

There were dissolved 1.74 g of 3-ethoxy-4-hydroxy-5-phenylthiomethylbenzaldehyde and 1.06 g of 1-phenyl-3,5-pyrazolidinedion in 60 ml of ethanol, to which 5 drops of piperidine was added, and the mixture was heated under reflux for 3 hours. After cooling, the reaction mixture was added with chloroform and washed with water and the solvent of the organic layer was distilled away. The residue was crystallized from ethanol to give 1.8 g of the compound (XXXI).
Yield: 67.2%.
Melting point: 84° to 84.5° C.

EXAMPLE 14

Preparation of the compound (XXXIII)

There were added 0.74 g (2 mmol) of 5-(p-bromophenylthiomethyl)ethylvanillin, 0.35 g (2 mmol) of 1-phenyl-3,5-pyrazolidinedion and a catalytic amount (2 to 3 drops) of pyridine to 50 ml of ethanol, and the mixture was heated under reflux for 6 hours in Dean-Stark apparatus. After cooling, the deposited crystals were filtered off from the reaction mixture, and the crystals were recrystallized from ethanol to give 0.88 g of the compound (XXXIII) as orange needles.
Yield: 83.2%.
Melting point: 187° to 189° C.

EXAMPLE 15

Preparation of the compound (XXXV)

There were added 0.63 g (2 mmol) of 3-butoxy-4-hydroxy-5-(phenylthiomethyl)benzaldehyde, 0.35 g (2 mmol) of 1-phenyl-3,5-pyrazolidinedion and a catalytic amount (2 to 3 drops) of pyridine to 50 ml of ethanol, and the mixture was heated under reflux for 6 hours in Dean-Stark apparatus. After cooling, the deposited crystals were filtered off from the reaction mixture, and the crystals were recrystallized from ethanol to give 0.66 g of the compound (XXXV) as orange needles.
Yield: 69.0%.
Melting point: 141° to 143° C.

What we claim is:

1. A 3-phenylthiomethylstyrene derivative having the formula (1):

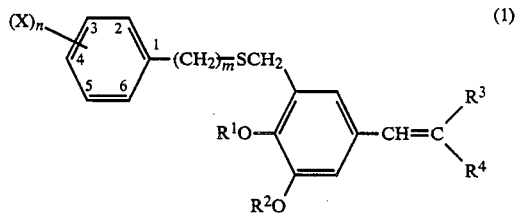

wherein X is hydrogen atom, an alkyl group having 1 to 5 carbon atoms, an alkoxyl group represented by the formula: $R^5O$ in which $R^5$ is an alkyl group having 1 to 3 carbon atoms, a nitro group, an amino group, a hydroxyl group, a halogen atom or an alkoxycarbonyl group represented by the formula: $COOR^6$ in which $R^6$ is an alkyl group having 1 to 3 carbon atoms; $R^1$ is hydrogen atom, an alkyl group having 1 to 3 carbon atoms or an acyl group represented by the formula: $R^7CO$ in which $R^7$ is phenyl group or an alkyl group having 1 to 3 carbon atoms; $R^2$ is hydrogen atom or an alkyl group having 1 to 5 carbon atoms; $R^3$ is a group represented by the formula: $COOR^8$ in which $R^8$ is hydrogen atom or an alkyl group having 1 to 4 carbon atoms or a carbamoyl group; $R^4$ is cyano group or an alkylsulfonyl group represented by the formula: $R^9SO_2$ in which $R^9$ is an alkyl group having 1 to 4 carbon atoms; $R^3$ and $R^4$ when taken together represent a group represented by the formula:

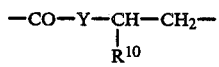

in which $R^{10}$ is hydrogen atom or an alkyl group having 1 to 4 carbon atoms and Y is oxygen atom or NH, a group represented by the formula:

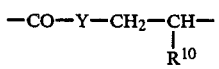

in which $R^{10}$ and Y are as defined above or a group represented by the formula:

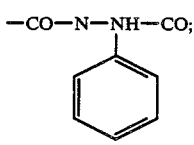

n is an integer of 1 to 5 when X is a halogen atom or 1 when X is a group other than the halogen atom; and m is 0 or an integer of 1 to 3, or a salt thereof with a base, when X is hydroxyl group, $R^1$ is hydrogen atom or $R^2$ is hydrogen atom.

2. The compounds of claim 1, wherein X is hydrogen atom.

3. The compounds of claim 1, wherein X is halogen atom.

4. The compounds of claim 1, wherein X is an alkoxyl group represented by the formula: $R^5O$ in which $R^5$ is as defined above.

5. The compounds of claim 1, wherein X is an alkyl group having 1 to 5 carbon atoms.

6. The compounds of claim 1, wherein $R^1$ is hydrogen atom.

7. The compounds of claim 1, wherein $R^2$ is hydrogen atom.

8. The compounds of claim 1, wherein $R^2$ is an alkyl group having 1 to 5 carbon atoms.

9. The compounds of claim 1, wherein $R^3$ is a group represented by the formula: $COOR^8$ in which $R^8$ is as defined above.

10. The compounds of claim 1, wherein $R^3$ is a carbamoyl group.

11. The compounds of claim 1, wherein $R^4$ is cyano group.

12. The compounds of claim 1, wherein $R^4$ is an alkylsulfonyl group represented by the formula: $R^9SO_2$ in which $R^9$ is as defined above.

13. The compounds of claim 1, wherein $R^3$ and $R^4$ are taken together and represent a group represented by the formula:

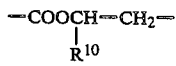

or a group represented by the formula:

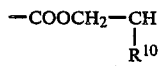

in which $R^{10}$ is as defined above.

14. The compounds of claim 1, wherein $R^3$ and $R^4$ are taken together and represent a group represented by the formula:

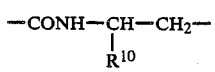

or a group represented by the formula:

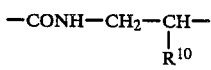

in which $R^{10}$ is as defined above.

15. The compounds of claim 1, wherein $R^3$ and $R^4$ are taken together and represent a group represented by the formula:

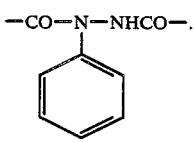

16. The compounds of claim 1, wherein X is hydrogen atom, $R^1$ is hydrogen atoms, $R^2$ is ethyl group, $R^3$ is $-COOC_2H_5$, $R^4$ is $-SO_2CH_3$, n is 1 and m is 0.

17. The compounds of claim 1, wherein X is hydrogen atom, $R^1$ is hydrogen atom, $R^2$ is ethyl group, $R^3$ is $-CONH_2$, $R^4$ is cyano group, n is 1 and m is 0.

18. The compounds of claim 1, wherein X is hydrogen atom, $R^1$ is hydrogen atom, $R^2$ is ethyl group, $R^3$ and $R^4$ are taken together and represent a group represented by the formula: $-CO-O-CH_2-CH_2-$, n is 1 and m is 0.

19. The compounds of claim 1, wherein X is hydrogen atom, $R^1$ is hydrogen atom, $R^2$ is ethyl group, $R^3$ and $R^4$ are taken together and represent a group represented by the formula:

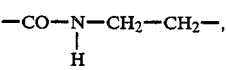

n is 1 and m is 0.

20. The compounds of claim 1, wherein X is hydrogen atom, $R^1$ is hydrogen atom, $R^2$ is ethyl group, $R^3$ and $R^4$ are taken together and represent a group represented by the formula:

n is 1 and m is 0.

21. The compounds of claim 1, wherein X, $R^1$ and $R^2$ are hydrogen atoms, $R^3$ is $-CONH_2$, $R^4$ is cyano group, n is 1 and m is 0.

22. The compounds of claim 1, wherein X is methoxy group attached at 4-position, $R^1$ is hydrogen atom, $R^2$ is ethyl group, $R^3$ is —$CONH_2$, $R^4$ is cyano group, n is 1 and m is 0.

23. The compounds of claim 1, wherein X is methoxy group attached at 2-position, $R^1$ is hydrogen atom, $R^2$ is ethyl group, $R^3$ is —$CONH_2$, $R^4$ is cyano group, n is 1 and m is 0.

24. The compounds of claim 1, wherein X are chlorine atoms attached at 2-position and 6-position, $R^1$ is hydrogen atom, $R^2$ is ethyl group, $R^3$ is —$CONH_2$, $R^4$ is cyano group, n is 2 and m is 0.

25. The compounds of claim 1, wherein X is hydrogen atom, $R^1$ is hydrogen atom, $R^2$ is methyl group, $R^3$ is —$CONH_2$, $R^4$ is cyano group, n is 1 and m is 0.

26. The compounds of claim 1, wherein X is chlorine atom attached at 4-position, $R^1$ is hydrogen atom, $R^2$ is ethyl group, $R^3$ is —$CONH_2$, $R^4$ is cyano group, n is 1 and m is 0.

27. The compounds of claim 1, wherein X are chlorine atoms attached at 3-position and 4-position, $R^1$ is hydrogen atom, $R^2$ is ethyl group, $R^3$ is —$CONH_2$, $R^4$ is cyano group, n is 2 and m is 0.

28. The compounds of claim 1, wherein X is t-butyl group attached at 4-position, $R^1$ is hydrogen atom, $R^2$ is ethyl group, $R^3$ is —$CONH_2$, $R^4$ is cyano group, n is 1 and m is 0.

29. The compounds of claim 1, wherein X are chlorine atoms attached at 3-position and 4-position, $R^1$ is hydrogen atom, $R^2$ is ethyl group, $R^3$ and $R^4$ taken together represent a group represented by the formula: —CO—O—$CH_2$—$CH_2$—, n is 2 and m is 0.

30. The compounds of claim 1, wherein X is bromine atom attached at 4-position, $R^1$ is hydrogen atom, $R^2$ is ethyl group, $R^3$ and $R^4$ are taken together and represent a group represented by the formula:

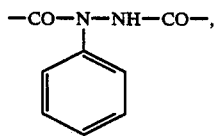

n is 1 and m is 0.

31. A pharmaceutical composition comprising an antiallergic effective amount of a 3-phenylthiomethylstyrene derivative having the formula (1):

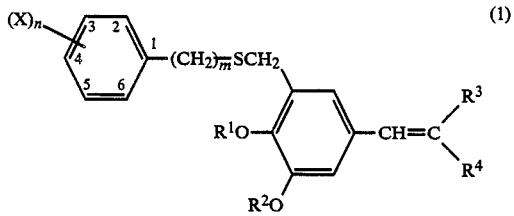

wherein X is hydrogen atom, an alkyl group having 1 to 5 carbon atoms, an alkoxyl group represented by the formula: $R^5O$ in which $R^5$ is an alkyl group having 1 to 3 carbon atoms, a nitro group, an amino group, a hydroxyl group, a halogen atom or an alkoxycarbonyl group represented by the formula: $COOR^6$ in which $R^6$ is an alkyl group having 1 to 3 carbon atoms; $R^1$ is hydrogen atom, an alkyl group having 1 to 3 carbon atoms or an acyl group represented by the formula: $R^7CO$ in which $R^7$ is phenyl group or an alkyl group having 1 to 3 carbon atoms; $R^2$ is hydrogen atom or an alkyl group having 1 to 5 carbon atoms; $R^3$ is a group represented by the formula: $COOR^8$ in which $R^8$ is hydrogen atom or an alkyl group having 1 to 4 carbon atoms or a carbamoyl group; $R^4$ is cyano group or an alkylsulfonyl group represented by the formula: $R^9SO_2$ in which $R^9$ is an alkyl group having 1 to 4 carbon atoms; $R^3$ and $R^4$ when taken together represent a group represented by the formula:

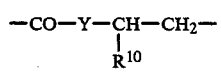

in which $R^{10}$ is hydrogen atom or an alkyl group having 1 to 4 carbon atoms and Y is oxygen atom or NH, a group represented by the formula:

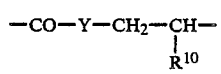

in which $R^{10}$ and Y are as defined above or a group represented by the formula:

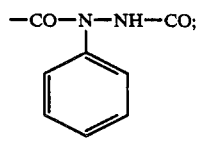

n is an integer of 1 to 5 when X is a halogen atom or is 1 when X is a group other than the halogen atom; and m is 0 or an integer of 1 to 3, or a pharmaceutically acceptable salt thereof; and a pharmaceutically acceptable carrier.

32. A pharmaceutical composition comprising a tyrosinekinase inhibiting effective amount of a 3-phenylthiomethylstyrene derivative having the formula (1):

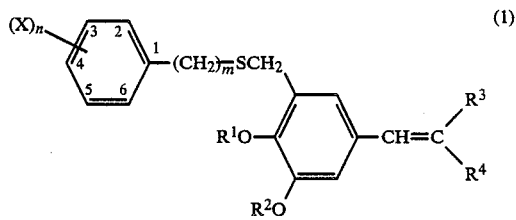

wherein X is hydrogen atom, an alkyl group having 1 to 5 carbon atoms, an alkoxyl group represented by the formula: $R^5O$ in which $R^5$ is an alkyl group having 1 to 3 carbon atoms, a nitro group, an amino group, a hydroxyl group, a halogen atom or an alkoxycarbonyl group represented by the formula: $COOR^6$ in which $R^6$ is an alkyl group having 1 to 3 carbon atoms; $R^1$ is hydrogen atom, on alkyl group having 1 to 3 carbon atoms or an acyl group represented by the formula: $R^7CO$ in which $R^7$ is phenyl group or an alkyl group having 1 to 3 carbon atoms; $R^2$ is hydrogen atom or an alkyl group having 1 to 5 carbon atoms; $R^3$ is a group represented by the formula: $COOR^8$ in which $R^8$ is hydrogen atom or an alkyl group having 1 to 4 carbon atoms or a carbamoyl group; $R^4$ is cyano group or an alkylsulfonyl group represented by the formula: $R^9SO_2$ in which $R^9$ is an alkyl group having 1 to 4 carbon atoms; $R^3$ and $R^4$ when taken together represent a group represented by the formula:

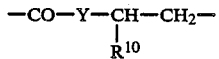

in which $R^{10}$ is hydrogen atom or an alkyl group having 1 to 4 carbon atoms and Y is oxygen atom or NH, a group represented by the formula

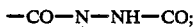

in which $R^{10}$ and Y are as defined above or a group represented by the formula:

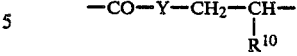

n is an integer of 1 to 5 when X is a halogen atom or 1 when X is a group other than the halogen atom; and m is 0 or an integer of 1 to 3, or a pharmaceutically acceptable salt thereof; and a pharmaceutically acceptable carrier.

33. A method of effecting an antiallergic response in a mammal which comprises administering to said mammal an antiallergic effective amount of a 3-phenylthiomethylstyrene derivative according to claim 1.

34. A method of effecting tyrosinekinase inhibition in a mammal which comprises administering to said mammal a tyrosinekinase inhibiting effective amount of a 3-phenylthiomethylstyrene derivative according to claim 1.

* * * * *